(12) United States Patent
Liang et al.

(10) Patent No.: US 10,000,790 B2
(45) Date of Patent: Jun. 19, 2018

(54) MATERIALS AND METHODS FOR RAPID VISUALIZATION OF NAD(P)H

(71) Applicants: Pingping Liang, Miami, FL (US); Haixiang Yu, Miami, FL (US); Yi Xiao, Miami, FL (US)

(72) Inventors: Pingping Liang, Miami, FL (US); Haixiang Yu, Miami, FL (US); Yi Xiao, Miami, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 303 days.

(21) Appl. No.: 14/752,970

(22) Filed: Jun. 28, 2015

(65) Prior Publication Data
US 2016/0376631 A1 Dec. 29, 2016

(51) Int. Cl.
*C12Q 1/32* (2006.01)

(52) U.S. Cl.
CPC ..................... *C12Q 1/32* (2013.01)

(58) Field of Classification Search
CPC .......................................... C12Q 1/32
USPC ................................. 435/26, 287.7
See application file for complete search history.

(56) References Cited

U.S. PATENT DOCUMENTS

| | | | | | |
|---|---|---|---|---|---|
| 4,387,990 | A | * | 6/1983 | Yazawa | G01N 21/8483 356/244 |
| 5,006,458 | A | * | 4/1991 | Kato | G01N 33/525 422/423 |
| 5,063,153 | A | * | 11/1991 | Arai | G01N 33/525 422/423 |
| 5,958,339 | A | * | 9/1999 | Belly | C01N 33/54386 422/422 |

(Continued)

FOREIGN PATENT DOCUMENTS

| | | |
|---|---|---|
| CN | 1821751 A | 8/2006 |
| WO | WO 2006/008742 A1 | 1/2006 |

OTHER PUBLICATIONS

El-Sayed, Ivan.H. et al. "Surface Plasmon Resonance Scattering and Absorption of anti-EGFR Antibody Conjugated Gold Nanoparticles in Cancer Diagnostics: Applications in Oral Cancer," *Nano Letters*, 2005, 5(5): 829-834.

(Continued)

*Primary Examiner* — Jill Alice Warden
*Assistant Examiner* — Julie L Tavares
(74) *Attorney, Agent, or Firm* — Saliwanchik, Lloyd & Eisenschenk

(57) ABSTRACT

The subject invention provides materials and methods for detecting the presence of an electron donor. In a specific embodiment, the device detects the presence of dihydronicotinamide adenine dinucleotide (NADH) via a colorimetric change output by the sensing device. In another specific embodiment, the presence of an enzyme capable of catalyz- (Continued)

ing, or an agent capable of inhibiting, the production of NADH can also be detected by a colorimetric readout using the same device. In some embodiments, dihydronicotinamide adenine dinucleotide phosphate (NADPH) can also be detected using the device provided herein. Advantageously, preferred embodiments of the subject invention provide a low-cost, sensitive device for monitoring the presence of critical biological analytes in a variety of applications.

19 Claims, 13 Drawing Sheets
(13 of 13 Drawing Sheet(s) Filed in Color)

(56) References Cited

U.S. PATENT DOCUMENTS

2010/0233708 A1* 9/2010 Mehra .................. G01N 33/558
435/6.11

OTHER PUBLICATIONS

Henglein, Arnim et al. "Physicochemical Properties of Small Metal Particles in Solution: "Microelectrode" Reactions, Chemisorption, Composite Metal Particles, and the Atom-to-Metal Transition," *J. Phys. Chem.*, 1993, 97: 5457-5471.

Ivanova, O.S., et al. "Electrochemical Size Discrimination of Gold Nanoparticles Attached to Glass/Indium-Tin-Oxide Electrodes by Oxidation in Bromide-Containing Electrolyte," *Analytical Chemistry*, 2010, 82:5844-5850.

Kobayashi, Yoshinori et al. "Purification and Properties of NAD-Dependent D-Glucose Dehydrogenase Produced by Alkalophilic *Corynebacterium* sp. No. 93-1," 1980, *Agric. Biol. Chem.*, 44(10):2261-2269.

Link, Stephan et al., "Size and Temperature Dependence of the Plasmon Absorption of Colloidal Gold Nanoparticles," *J. Phys. Chem. B*, 1999, 103: 4212-4217.

Medley, C.D. et al. "Gold Nanoparticles-Based Colorimetric Assay for the Direct Detection of Cancerous Cells," *Analytical Chemistry*, 2008, 80(4):1067-1072.

Murphy, Catherine, et al. "Gold Nanoparticles in Biology: Beyond Toxicity to Cellular Imaging," *Accounts of Chemical Research*, 2008, 41: 1721-1730.

Qian, Kun et al. "Surface Plasmon-Driven Water Reduction: Gold Nanoparticle Size Matters," *Journal of the American Chemical Society*, 2014, 136: 9842-9845.

Saha, Krishnendu et al. "Gold Nanoparticles in Chemical and Biological Sensing," *Chemical Reviews*, 2012, 112(5); 2739-2779.

Sreeprasad, T.S., "Body- or Tip-Controlled Reactivity of Gold Nanorods and Their Conversion to Particles through Other Anisotrophic Strucures," *Langmuir*, 2007, 23: 9463-9471.

Valden, M. et al. "Onset of Catalytic Activity of Gold Clusters on Titania with the Appearance of Nonmetallic Properties," *Science*, 1998, 281: 1647-1650.

Rodríguez-Fernàndez, Jessica, Spatially-Directed Oxidation of Gold Nanoparticles by Au(III)—CTAB Complexes, *Journal of Physical Chemistry B*, 2005, 109:14257-14261.

Wu, Zhuangchun, et al."Transparent, Conductive Carbon Nanotube Films," *Science*, 2004, 305(5688)1273-1276.

Xiao, Yi et al. Catalytic Growth of Au Nanoparticles by NAD(P)H Cofactors: Optical Sensors for NAD(P)+-Dependent Biocatalyzed Transformations, *Angewandte Chemie*, 2004, 116(34): 4619-4622.

Zhang, Maogen et al. "Carbon Nanotube-Chitosan System for Electrochemical Sensing Based on Dehydrogenase Enzymes," *Analytical Chemistry*, 2004, 76:5045-5050.

* cited by examiner

Without wax barrier
With wax barrier
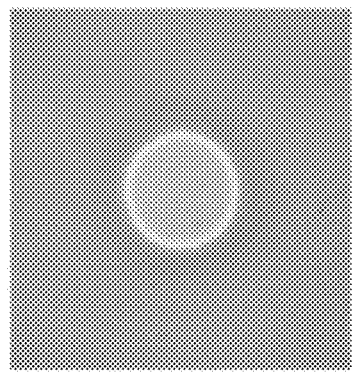
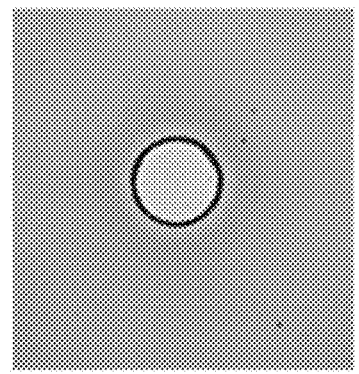
(A)
(B)
FIG. 12A
FIG. 12B
Absorbent
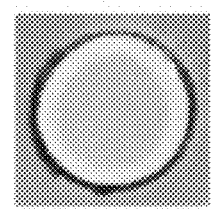
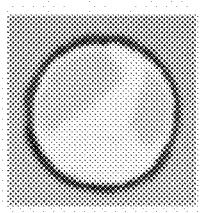
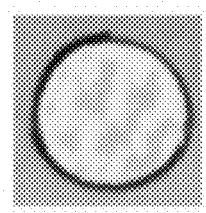
No absorbent  Rice paper   Paper towel
FIG. 13A     FIG. 13B     FIG. 13C
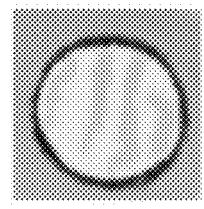
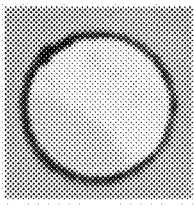
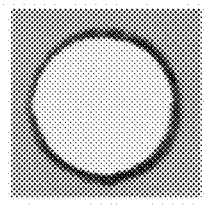
Kimwipe     Copy paper    Cotton
FIG. 13D     FIG. 13E     FIG. 13F

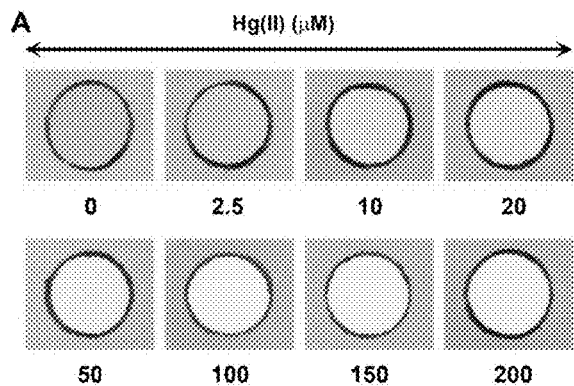
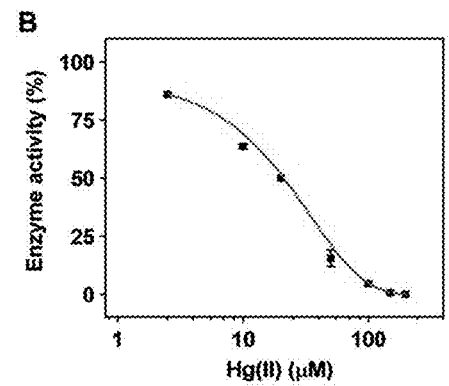
FIG. 17A     FIG. 17B
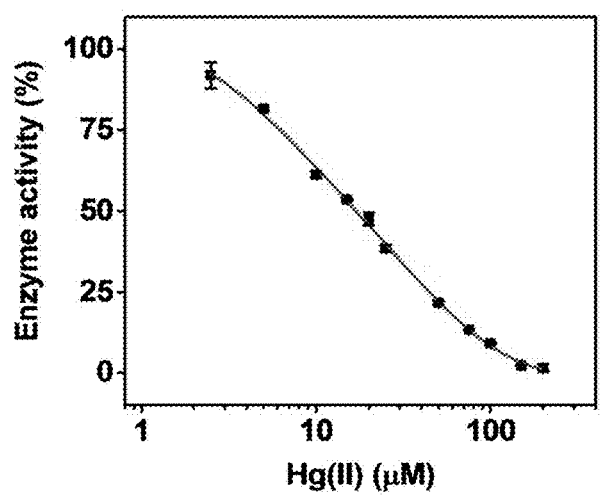
FIG. 18

MATERIALS AND METHODS FOR RAPID VISUALIZATION OF NAD(P)H

BACKGROUND OF INVENTION

Dihydronicotinamide adenine dinucleotide (phosphate) (NAD(P)H) and its oxidized form, nicotinamide adenine dinucleotide (phosphate) (NAD(P)$^+$) are ubiquitous biomolecules associated with cellular energy metabolism in both eukaryotic and prokaryotic organisms.[1] It has been reported that the NAD(P)$^+$/NAD(P)H couples are essential cofactors for more than 300 dehydrogenases.[2,3] Increased activity of dehydrogenases such as aldehyde dehydrogenases has been reported in various human cancers[4] and has been found to interfere with certain chemotherapeutic treatments.[5,6] Accordingly, dehydrogenase inhibitors have been developed for the treatment of human diseases,[4,5,7] as well as applications in alcohol dependence,[8] cocaine addiction,[9] anxiety,[10] and as resensitizing agents for cancers.[11] Thus, the development of sensitive and specific NAD(P)H sensors could not only open numerous possibilities for dehydrogenase characterization but also identify inhibitors of dehydrogenases for the development of novel anticancer agents,[12] antibiotics,[13] and pesticides.[14]

Gold nanoparticles (AuNPs) have been widely used for applications in sensing, catalysis, imaging, diagnostics, therapy and drug delivery due to their unique optical and electronic properties and good biological compatibility.[15-21] The properties of AuNPs usually depend on their size and shape,[22-26] and the dissolution of gold has proven to be an effective way to resize or reshape these particles.[27] Traditionally, colorimetric detection of NADH is based on the growth of gold nanoparticles, which requires a large sample volume, a longer reaction time, as well as sophisticated analytical instruments to confirm detection efficacy. See, for example, PCT Publication WO2006008742 and Chinese Publication CN1821751A.

Therefore, there still remains a need for diagnostic devices and methods that require less sample volume and easier method of fabrication, while maintaining the sensitivity for detecting analytes critical for biological activities in various applications.

BRIEF SUMMARY

The subject invention provides materials and methods for detecting the presence of an electron donor. In a specific embodiment, the device detects the presence of dihydronicotinamide adenine dinucleotide (NADH) via a colorimetric change output by the sensing device. In another specific embodiment, the presence of an enzyme capable of catalyzing, or an agent capable of inhibiting, the production of NADH can also be detected by a colorimetric readout using the same device. In some embodiments, dihydronicotinamide adenine dinucleotide phosphate (NADPH) can also be detected using the device provided herein.

Advantageously, preferred embodiments of the subject invention provide a low-cost, sensitive device for monitoring the presence of critical biological analytes in a variety of applications.

In one aspect, the subject invention provides a device for detecting the presence of an electron donor, comprising a first cover layer, at least one testing zone provided on a porous membrane and exposed by a void in the first cover layer, each testing zone comprising a surface immobilized with metallic nanoparticles thereon, and a second cover layer provided beneath the porous membrane. In a preferred embodiment, the device further comprises an absorbent layer, which is provided between the porous membrane and the second cover layer.

In some embodiments, the subject invention provides a paper-based device comprising at least one testing zone within which the mechanism of detection occurs. Preferably, each testing zone is provided on a porous membrane impermeable to the metallic nanoparticles. In certain embodiments, the testing zone is confined by a closed barrier impermeable to the sample.

In some embodiments, the sample being analyzed comprises at least one surfactant and at least one salt, the salt comprising ions of the same metal as the nanoparticles immobilized atop the testing zone. In an exemplary embodiment, the surfactant is cetyltrimethylammonium bromide (CTAB). In specific embodiments, the metal is selected from gold, silver, copper, and platinum. In a preferred embodiment, the nanoparticles comprise gold and the salt comprises gold(III) ions.

In certain embodiments, the sample optionally comprises an electron acceptor and an enzyme/enzyme substrate pair capable of catalyzing the production of the electron donor. In other embodiments, the sample further comprises, in addition to an electron acceptor and an enzyme/enzyme substrate pair, an agent for inhibiting the enzymatic reaction that produces the electron donor.

In some embodiments, the device provided herein is capable of detecting less than 200, 150, 100, 75, 50 or 25 µM of NAD(P)H. In a preferred embodiment, the device is capable of detecting about 12.5 µM of NAD(P)H. In a particularly preferred embodiment, the device is capable of detecting about 12.5 µM in less than 4 minutes.

In another aspect, the subject invention provides a method of detecting the presence of an electron donor, comprising providing the detection device described herein, providing a sample for at least one testing zone of the device, the sample comprising at least one surfactant and at least one salt of the same metal as the nanoparticles, and observing any colorimetric change of each testing zone in contact with the sample. Advantageously, in preferred embodiments of the invention, any colorimetric change occurring in a testing zone can be directly observed with the naked eyes. Alternatively, other methods of detecting light absorbance of the sample may be employed.

In yet another aspect, the subject invention provides an advantageous device for detecting the presence of NAD(P)H in a sample, comprising a first cover layer, at least one testing zone provided on mixed cellulose ester paper and exposed by a void in the first cover layer, each testing zone comprising a surface immobilized with gold nanoparticles thereon and bound by a closed barrier substantially impermeable to the sample, an absorbent layer provided beneath the mixed cellulose ester paper, and a second cover layer provided beneath the absorbent layer.

In an exemplary embodiment, the sample comprises cetyltrimethylammonium bromide and Au (III) ions provided by a metallic salt of gold.

Alternatively, the device can also be used to detect the presence of an enzyme/enzyme substrate pair catalyzing, or an inhibitor preventing, the production of NAD(P)H in a sample.

Other objects, features, and advantages of the invention will be apparent to those skilled in the art from the detailed description of the invention which will now follow, taken in conjunction with the tables, drawings, and the accompanying claims.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

FIG. 12A shows the diffusion of a droplet of 25 μL of 200-μM $Au^{3+}$-CTAB solution on an MCE filter paper without a wax-circled testing zone at room temperature. FIG. 12B depicts the same experiment except that the testing zone was circled with a wax barrier. The intensity of the readouts in the testing zones was measured with ImageJ software and AuNP dissolution was calculated by normalizing the intensity of the AuNP film alone to 0% and the intensity of the MCE filter paper to 100%.

FIGS. 13A-13F represent the performance of no absorbent layer, rice paper, paper towel, Kimwipe, copy paper, and cotton, respectively, as various absorbent layer materials in distributing $Au^{3+}$-CTAB complexes over the testing zone. Each assembly was tested with 25 μL of 200 μM $Au^{3+}$-CTAB for 4 min at room temperature.

FIG. 17A demonstrates the results of using an exemplary paper-based device to measure NADH production by 0.1 U GDH in a 25 μL sample comprising 0-200 μM Hg(II) in 400 μM of $Au^{3+}$-CTAB after a 4-min reaction. FIG. 17B depicts the intensity of the readouts in the testing zones measured with ImageJ software, and the enzyme activity was calculated by normalizing the unreacted AuNP film to 100% and the fully dissolved AuNP-coated film in the presence of 200 μM of Hg(II) to 0%. The calculated $IC_{50}$ value was 20 μM.

FIG. 18 shows the inhibitory effects of Hg(II) on GDH activity in homogenous solution. The absorbance change at 340 nm was monitored to calculate enzyme activity. Hg(II) concentrations being tested ranged from 0-200 μM. The enzyme's activity was defined as 100% in the absence of the Hg(II) ion, and as the Hg(II) concentration increased the enzyme's activity decreased. The calculated $IC_{50}$ value was 18 μM.

DETAILED DESCRIPTION

Figure 1:
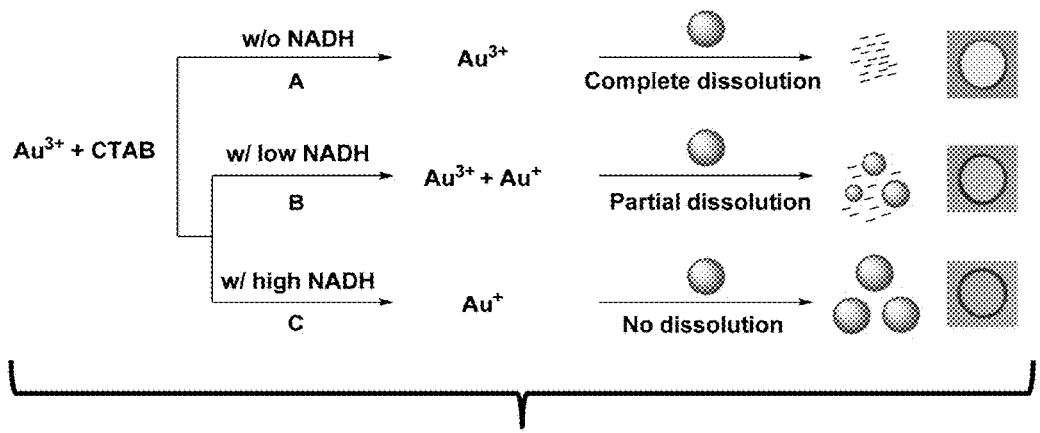
FIG. 1 shows the process of colorimetric visualization of NAD(P)H with a paper-based sensor. Citrate-coated AuNPs (4.4±1.6-nm diameter) are deposited on mixed cellulose ester (MCE) filter paper via ambient vacuum filtration, forming a red AuNP-coated layer. In the absence of NADH, $Au^{3+}$-CTAB completely dissolves the AuNP coating, yielding a white readout. In the presence of 50 μM NADH (i.e. "low NADH"), partial reduction of $Au^{3+}$ by NADH resulted in only partial dissolution of AuNPs, giving rise to a light pink color. When 200 μM NADH (i.e. "high NADH") was added, all of the $Au^{3+}$ was reduced by NADH, leaving the AuNPs intact and producing a red readout.

In the following detailed description, reference is made to the accompanying drawings, depicting exemplary, non-limiting and non-exhaustive embodiments of the invention. These embodiments are described in sufficient detail to enable those having skill in the art to practice the invention, and it is understood that other embodiments may be used, and other changes may be made, without departing from the spirit or scope of the invention. The following detailed description is, therefore, not to be taken in a limiting sense, and the scope of the invention is defined only by the appended claims. All patents, patent applications, provisional applications, and publications referred to or cited herein are incorporated by reference in their entirety, including all figures and tables, to the extent they are not inconsistent with the explicit teachings of this specification.

The subject invention provides materials and methods for detecting the presence of an electron donor. In a specific embodiment, the device detects the presence of dihydronicotinamide adenine dinucleotide (NADH) via a colorimetric change output by the sensing device. In another specific embodiment, the presence of an enzyme capable of catalyzing, or an agent capable of inhibiting, the production of NADH can also be detected by a colorimetric readout using the same device. In some embodiments, dihydronicotinamide adenine dinucleotide phosphate (NADPH) can also be detected using the device provided herein. Advantageously, preferred embodiments of the subject invention provide a low-cost, sensitive device for monitoring the presence of critical biological analytes in a variety of applications.

In one aspect, the subject invention provides a device for detecting the presence of an electron donor, comprising a first cover layer, at least one testing zone provided on a porous membrane and exposed by a void in the first cover layer, each testing zone comprising a surface immobilized with metallic nanoparticles thereon, and a second cover layer provided beneath the porous membrane.

In some embodiments, the sample being analyzed comprises at least one surfactant and at least one salt, the salt comprising ions of the same metal as the nanoparticles immobilized atop the testing zone. In an exemplary embodiment, the surfactant is cetyltrimethylammonium bromide (CTAB). Other surfactants comprising CTA and a halogen-based counterion, such as $Cl^-$, $F^-$, and $I^-$, are also available as alternative embodiments of the subject invention. The metal of choice provided herein is selected from transition metals including, but not limited to, gold, silver, copper, and platinum. In a preferred embodiment, the nanoparticles comprise elemental gold ($Au^0$), hereafter referred to as AuNPs, and the metallic salt comprises gold (III) ($Au^{3+}$) ions.

In some embodiments, the electron donor is a cofactor involved in an enzymatic reaction capable of inhibiting the dissolution of the metallic nanoparticles in the presence of the ion-surfactant complex. In an exemplary embodiment, $Au^{3+}$ and CTAB form $AuBr_4^-$ in solution and, in the absence of the electron donor NAD(P)H, readily dissolve the AuNPs immobilized atop the testing zone, yielding a white-colored readout from the device. However, when an electron donor such as NAD(P)H is present in the same solution with the $AuBr_4^-$ complex, the dissolution of AuNPs is significantly inhibited, as indicated by a gradual change from white to red in the colorimetric readout of the device with increasing addition of NAD(P)H to the sample.

In certain embodiments, the sample being analyzed can further comprise an electron acceptor and an enzyme/enzyme substrate pair capable of catalyzing the production of the electron donor to be detected. As a result, the subject invention also provides an advantageous device for detecting the presence of either member of an enzyme/enzyme substrate pair.

As an exemplary embodiment of the subject invention, the electron donor is NADH, reduced from nicotinamide adenine dinucleotide ($NAD^+$) in the presence of glucose dehydrogenase (the enzyme) and glucose (the enzyme substrate). The conversion from $NAD^+$ to NADH can be accomplished by a number of dehydrogenase enzyme/enzyme substrate pairs including, but not limited to, glucose dehydrogenase/glucose, pyruvate dehydrogenase/pyruvate, malate dehydrogenase/malate, isocitrate dehydrogenase/isocitrate, and α-ketoglutarate dehydrogenase/α-ketoglutarate.

Furthermore, the presence of any agents inhibiting the production of the electron donor can also be realized if such agents exist in the sample along with the enzyme/enzyme substrate pair. Non-limiting examples of enzymatic inhibitors provided herein include, but are not limited to, silver (I) and mercury (II), cobalt(II), copper(II), iron(III), iron(II) and nickel(II).

In some embodiments, the subject invention provides a paper-based device comprising at least one testing zone within which the detection of the electron donor occurs. Each testing zone is provided on a porous membrane impermeable to the metallic nanoparticles and exposed to the sample by a void on the first cover layer. In a preferred embodiment, the porous membrane comprises mixed cellulose ester (MCE) paper. Other suitable membrane materials available for alternative embodiments of the subject invention include, but are not limited to, polyamide, polycarbonate, polyethersulfone, polyvinylidene fluoride, nylon, nitrocellulose, and polypropylene.

In certain embodiments, the first and the second cover layers comprise substantially the same material which is preferably impermeable to the sample. In a preferred embodiment, each cover layer comprises, as its major component, polyvinyl chloride. Advantageously, multiple testing zones can be provided on a single porous membrane, each testing zone exposed by a void in the first cover layer, allowing high through-put detection of one or more samples simultaneously.

Optionally, the testing zone is confined by a closed barrier impermeable to the sample, the barrier comprising a substance substantially insoluble in water. In a preferred embodiment, the substance comprises wax, and the barrier is formed by applying an enclosed circle of wax around the testing zone. Other substances and methods of applying the substances resulting in the prevention of lateral diffusion of the sample across the barrier are also available as alternative embodiments of the subject invention.

In an effort to further restrict the lateral diffusion of the sample, certain embodiments of the subject invention provide a device further comprising an absorbent layer disposed between the porous membrane and the second cover layer. The absorbent layer serves to enhance the capillary force mediating the diffusion of the sample through the thickness of the testing zone. A preferred embodiment of the invention provides that the absorbent layer comprises cotton.

In some embodiments, the device provided herein is capable of detecting less than 200, 150, 100, 75, 50 or 25 µM of NAD(P)H. In a preferred embodiment, the device is capable of detecting about 12.5 µM of NAD(P)H. In a particularly preferred embodiment, the device is capable of detecting about 12.5 µM in less than 4 minutes.

In another aspect, the subject invention provides a method of detecting the presence of an electron donor, comprising providing the detection device disclosed herein, providing a sample for at least one testing zone of the device, the sample comprising at least one surfactant and at least one salt of the same metal as the nanoparticles, and observing any colorimetric change of each testing zone in contact with the sample.

Any suitable method for providing the sample at the testing zone of the device may be used in accordance with embodiments of the invention. For example, suitable methods include pipetting, rinsing, dipping, immersing, or any combination thereof. In a preferred embodiment, the sample solution is pipetted onto the testing zone.

Advantageously, in preferred embodiments, any colorimetric change presented in the testing zone can be directly observed with the naked eyes. In a preferred embodiment, the dissolution of AuNPs by the $Au^{3+}$-CTAB complex results in a white readout within the testing zone of the device; however, upon adding NAD(P)H, a colorimetric change to a red shade is readily visualized by the naked eyes. Alternatively, other methods of optically detecting light absorbance of the sample may be employed.

In yet another aspect, the subject invention provides an advantageous device for detecting the presence of NAD(P)H in a sample, comprising a first cover layer, at least one testing zone provided on mixed cellulose ester paper and exposed by a void in the first cover layer, each testing zone comprising a surface immobilized with gold nanoparticles thereon and bound by a closed barrier substantially impermeable to the sample, an absorbent layer provided beneath the mixed cellulose ester paper, and a second cover layer provided beneath the absorbent layer.

In an exemplary embodiment, the sample comprises cetyltrimethylammonium bromide and gold (III) ions provided by a metallic salt of gold.

Alternatively, the device can also be used to detect the presence of an enzyme/enzyme substrate pair catalyzing, or an inhibitor preventing, the production of NAD(P)H in a sample.

Advantageously, the subject invention provides materials and methods to rapidly screen the presence of an electron donor capable of modulating redox reaction between metallic nanoparticles and their corresponding ions, the result of such reaction being readily visualized by the naked eyes.

Furthermore, preferred embodiments of the device provided herein are useful for detecting the presence of a wide variety of dehydrogenase enzyme/enzyme substrate pairs and inhibitors of these enzymatic reactions in applications such as on-site drug testing and choline or organophosphorus neurotoxin detection.

Materials and Methods

Gold(III) chloride trihydrate, trisodium citrate dihydrate, sodium borohydride ($NaBH_4$), cetyltrimethylammonium bromide (CTAB), dihydronicotinamide adenine dinucleotide (NADH), nicotinamide adenine dinucleotide ($NAD^+$), glucose, glucose dehydrogenase (from *Pseudomonas* sp.), mercury(II) acetate, lead(II) acetate trihydrate, tryptone, sodium cloride (NaCl), yeast extract, silver nitrate and phosphate buffer solution (1.0 M, pH 7.4) were purchased from commercial sources and used as received. All solutions were prepared with deionized water. Wild type *E. coli* strain K12 was prepared as cell lysate and used in experiments.

4-nm AuNPs were synthesized by adding 0.5 mL 0.01 M $HAuCl_4$ and 0.5 mL of 0.01 M trisodium citrate solution to 18 mL of deionized water with stirring. 0.5 mL of ice-cold, freshly prepared 0.1 M $NaBH_4$ was added to the solution and stirring was immediately stopped. At this point, the solution turned orange-red.[28] The newly-synthesized AuNPs were used within 2-5 hours of preparation. The concentration of AuNPs was determined based on their extinction coefficient constant with a UV-Vis spectrometer (Cary 100, Varian). Particle size was characterized by transmission electron microscopy (TEM).

To observe the dissolution of AuNPs in the $Au^{3+}$-CTAB solution, an Amicon Ultra Centrifugal Filter (Millipore) was used to concentrate the as-prepared AuNPs at 1500 rcf (Eppendorf 5430R), obtaining a 6.6-fold concentrated solution of AuNPs. 328 picomoles of concentrated AuNPs was then added into a 44.4 mM of CTAB solution (pH 4) comprising 160 nanomoles of $Au^{3+}$, and the UV-Vis spectra were recorded for an hour at room temperature. The dissolution was very fast during the first 10 mM and started to reach its plateau after 40 min. To test the effects of $Au^{3+}$ concentration on AuNPs dissolution, 0-200 µM of gold salt in CTAB solution was added to identical aliquots of AuNPs (328 picomoles) and incubated for 40 min at room temperature while the UV-Vis spectra were being recorded. AuNP dissolution in solutions comprising different concentrations of NADH were also tested, the solutions being freshly prepared before each use. These solutions were mixed with 200 µM of gold salt solution and 328 picomoles of AuNPs was subsequently added into this mixture, followed by the recording of the UV-Vis spectra of samples after 40 min at room temperature. MCE membrane substrate (Millipore, 47-mm diameter, 100-nm pore size and 100-µm thickness) was pre-wetted with deionized water on a Kontes 47-mm Ultra-Ware Microfiltration support base (Kimble Chase). A 1.9 mL (771.4 picomoles) of freshly-made, citrate-capped AuNP solution diluted with 3.1 mL of 256 µM of sodium citrate was added to the funnel, and the film was subsequently prepared via ambient vacuum filtration. The film was then cut into 20 small pieces (5 mm W×6 mm L) after air-drying for 20 min, resulting in strips of film each coated with 21 picomoles AuNPs. These were dropped into 200 µM of Au$^{3+}$-CTAB solution comprising different concentrations of NADH and then photographed after 40 min.

After preparing the film, a wax pencil (Phano China Marker, Fisher Scientific) was used to draw circles (5 mm diameter) on the AuNP-coated film. The film was then cut into 9 pieces (8 mm W×8 mm L). A device was fabricated to comprise four layers (FIG. 3), listed here from top to bottom: a polyvinyl chloride plastic cover layer (4.4 cm W×5.4 cm L) with a 6-mm diameter hole on the top, a pre-wetted wax-circled AuNP-coated filter paper, a pre-wetted layer of hydrophilic cotton absorbent padding with Kimwipe paper, and a bottom plastic cover. The four layers were clamped together at the edges of the device with paper clips. 25 µL of 200 µM Au$^{3+}$-CTAB solution containing different concentrations of NADH were added into the wax circled testing zone, and the color change was visualized after 4 min. Intensity analysis was performed using the ImageJ software.

Figure 4A:
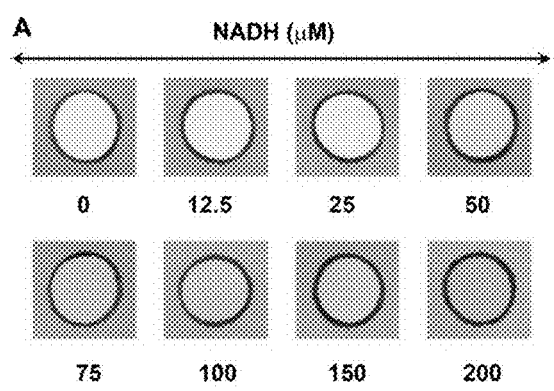
FIG. 4A demonstrates the detection of NADH in 25 μL of sample solutions using the exemplary device, the solutions comprising multiple concentrations of NADH in 200 μM $Au^{3+}$-CTAB solution at room temperature, on the exemplary paper-based device.
Figure 4B:
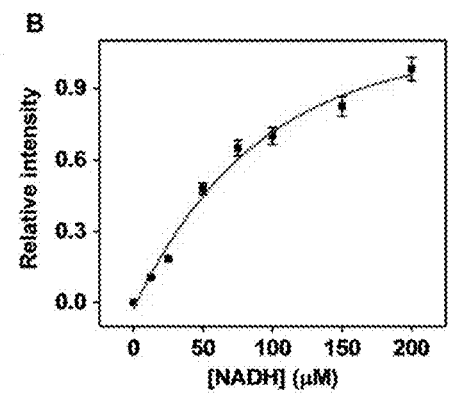
FIG. 4B shows the relative intensity of each testing zone's readout calculated by normalizing the unreacted AuNP-coated film to 1 and the AuNP-coated film in the absence of NADH to 0 using ImageJ software.
Figure 15A:
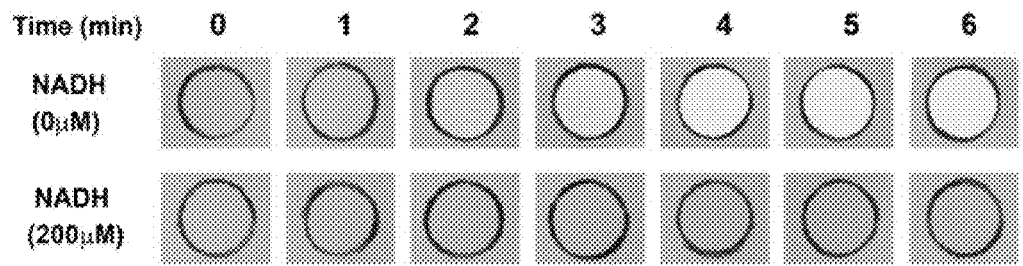
FIG. 15A depicts the colorimetric change in 25 μL samples at room temperature on a paper-based device in the absence (0 μM) and presence (200 μM) of NADH in a 200 μM of $Au^{3+}$-CTAB solution.
Figure 15B:
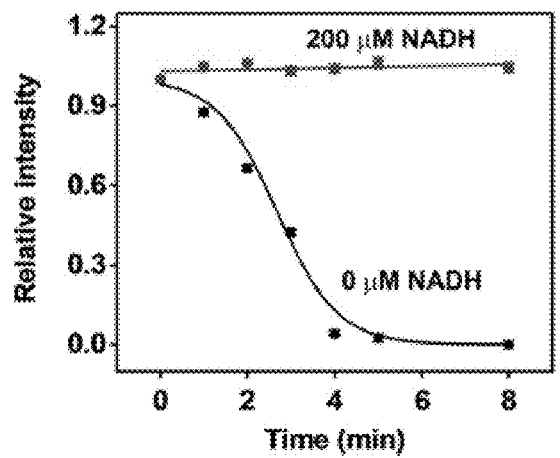
FIG. 15B is a graph showing the time course of the change in color intensity corresponding to the absence and presence of NADH on the paper-based device. The relative intensity of each testing zone's readout was calculated by normalizing the unreacted AuNP-coated film to 1 and the AuNP-coated film in the absence of NADH to 0 using ImageJ software.

This device allows the visualization of the presence of NADH at room temperature (FIG. 4A). The time-course demonstrated that a complete dissolution of AuNPs within this device was obtained after 4 minutes (FIGS. 15A and 15B). Under optimized experimental conditions, the lowest concentration of NADH that can be clearly visualized on our paper-based device is 12.5 µM in 4 min. Using the ImageJ software, the intensity of the color in the testing zone was measured and the normalized intensity for different concentrations of NADH was plotted (FIG. 4B).

Figure 3:
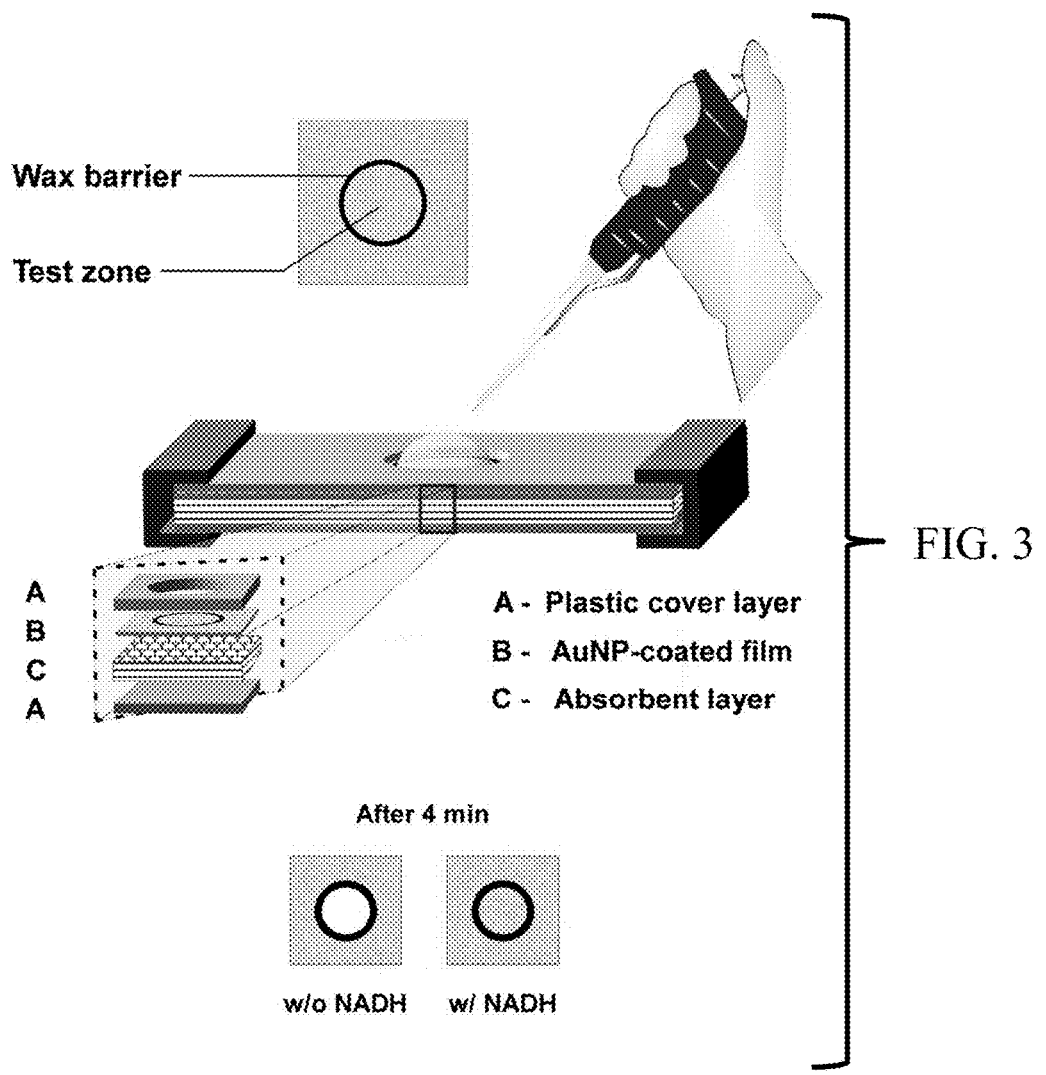
FIG. 3 is an exemplary schematic of a paper-based device for colorimetric detection of NADH in a microliter-scale sample. According to a specific embodiment, the device comprises an upper plastic cover layer with a hole exposing the underlying testing zone, a cotton absorbent layer, and a lower plastic cover layer. 25 μL of sample solution was added to the testing zone, which was confined within the wax circle on the AuNP-coated paper.

0.1 U glucose dehydrogenase (GDH) was combined with different concentrations (0-20 mM) of glucose in 0.1 M of phosphate buffer solution (pH 7.4) at 25° C., mixed with 400 µM of Au$^{3+}$-CTAB, and the subsequent mixture was applied to the paper-based device for a 4-min reaction, as shown in FIG. 3.

To test the inhibitory effects of Hg(II), different concentrations of Hg(II) was incubated with 0.1 U GDH for 10 min in the presence of 10 mM of glucose and 0.1 M of phosphate buffer solution (pH 7.4) at 25° C., then 6 mM of NAD' was added to initiate the enzymatic reaction for 15 mM. The kinetics of the reaction was monitored for the first 6 minutes in a microplate reader to calculate the enzyme's activity. 10 µL of the enzymatic reaction solution were added to 90 µL of 400 µM Au$^{3+}$-CTAB solution, and 25 µL of this solution was applied to the device test zone.

The colorimetric results were visualized after 4 minutes and evaluated for the inhibitory effects of these metals by measuring the decrease in the color intensity produced by the enzyme-substrate reaction. Ag(I) and Pb(II) were also tested as potential inhibitors in a similar fashion. Intensity analysis was performed using the ImageJ software.

Following are examples that illustrate procedures for practicing the invention. These examples should not be construed as limiting.

EXAMPLE 1

Figure 7A:
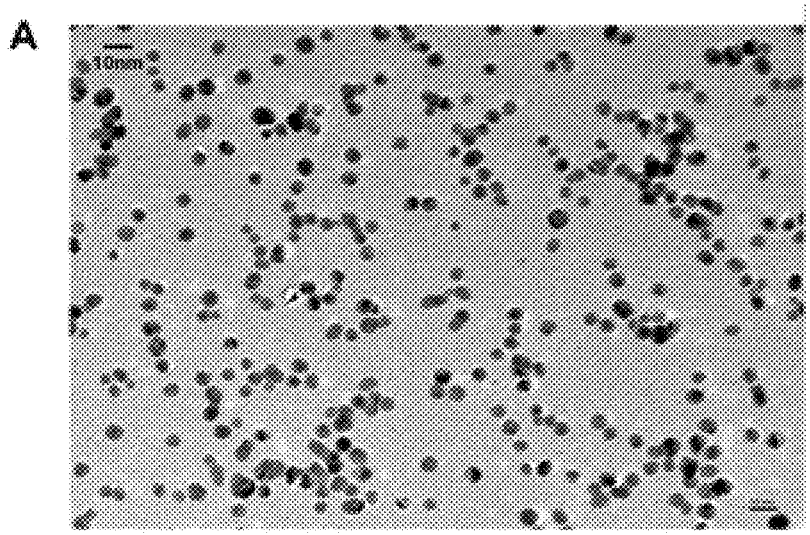
FIG. 7A is a TEM image of the 4.4 nm AuNPs.
Figure 7B:
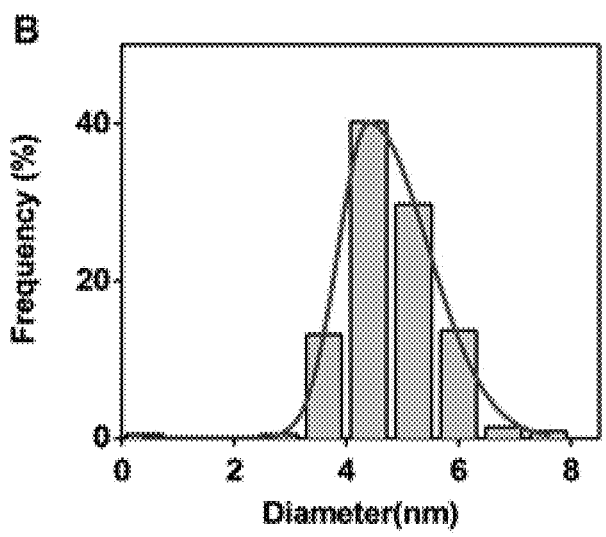
FIG. 7B shows the size distribution of synthesized AuNPs. The size measurement was performed using Nano Measurer 1.2.

To achieve a short reaction time, AuNPs with a 4-nm diameter were used as the signaling reporter because the AuNPs with smaller diameters are dissolved faster.[29,30] Citrate-capped AuNPs were synthesized and then concentrated to 2.67 µM. The particles were characterized by transmission electron microscopy (TEM) and the analysis of image confirmed that the unifounly sized AuNPs have a diameter of approximately 4.4±1.6 nm (FIGS. 7A and 7B). AuNP dissolution requires a CTAB concentration that is greater than its critical micelle concentration[31] to form micelles that carry Au$^{3+}$ ions.

Figure 8A:
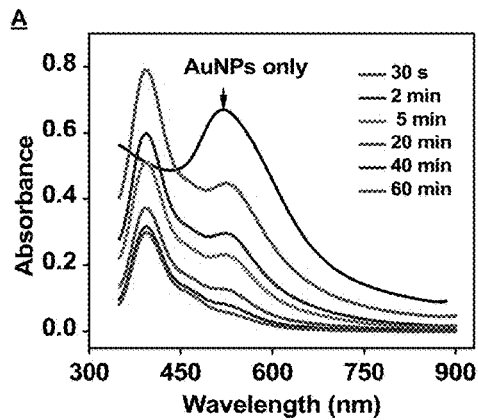
FIG. 8A shows the UV-Vis spectra recorded at different time points after adding 328 picomoles AuNPs into 44.4 mM of CTAB solution (pH 4) in the presence of 160 μM of $Au^{3+}$. Black line represents the spectrum after 60 min for AuNPs in CTAB without $Au^{3+}$.
Figure 8B:
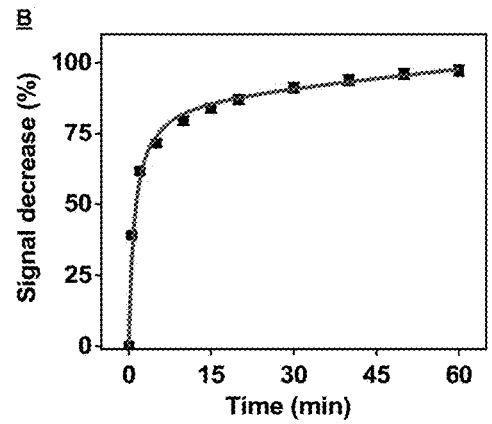
FIG. 8B shows the time-course of the decrease in absorbance at 526 nm. AuNPs in CTAB solution without $Au^{3+}$ was used as a reference to calculate the relative decrease in absorbance.
Figure 9A:
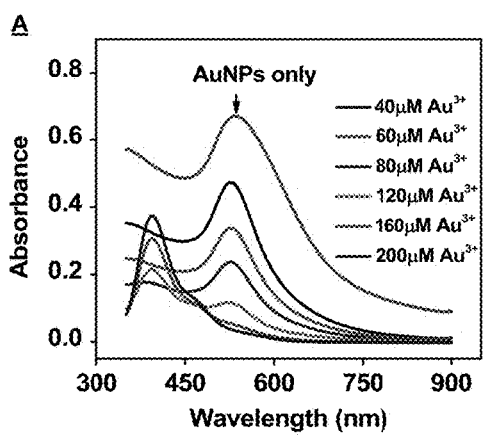
FIG. 9A depicts the UV-Vis spectra of 328 picomoles of AuNPs in the presence of $Au^{3+}$ concentrations ranging from 0-200 μM.
Figure 9B:
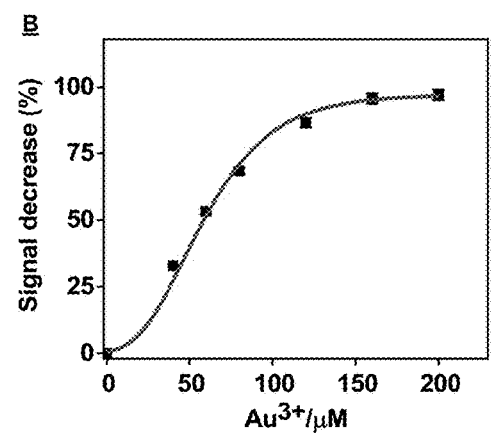
FIG. 9B shows that absorbance at 526 nm steadily decreased as the concentration of $Au^{3+}$ increased. AuNPs in CTAB solution without $Au^{3+}$ was used as a reference to calculate the relative decrease in absorbance.

When 160 nanomoles of Au$^{3+}$ was added into a 44.4 mM of CTAB solution (pH 4.0), the Au$^{3+}$-CTAB complex—more specifically, the AuBr$_4^-$ anion—exhibited strong absorbance at 394 nm with a distinct shoulder at 450 nm, as predicted.[32] Upon adding 328 picomoles of AuNPs, it was observed that the plasmon peak of the AuNPs shifted from 504 nm to 526 nm in the Au$^{3+}$-CTAB solution. The absorbance of both the Au$^{3+}$-CTAB complex at 394 nm and the AuNPs at 526 nm gradually decreased over the course of the reaction (FIG. 8A). Under reaction conditions where the Au$^{3+}$:AuNP ratio was 489:1, it was found that the absorbance at 526 nm decreased very rapidly during the first 10 min and started to reach a plateau after 40 min. No detectable change was observed after 60 min, clearly indicating that all AuNPs were dissolved (FIG. 8B). In contrast, no dissolution of AuNPs in CTAB solution was observed in the absence of Au$^{3+}$, and as a result, this was used as a reference to calculate the relative absorbance decrease at 526 nm. The concentration of Au$^{3+}$ plays an important role in AuNP dissolution. It was therefore sought to optimize the Au$^{3+}$: AuNP ratio in a homogeneous solution to achieve a much shorter reaction time. Specifically, samples were prepared by adding different concentrations of Au$^{3+}$ to identical aliquots of AuNPs and allowing the reaction to progress for 40 min. After the reaction was completed, the UV-Vis spectra were recorded. The results showed that AuNP dissolution increased with increasing Au$^{3+}$ concentration. Compared with AuNPs alone, the absorbance at 526 nm was greatly decreased but still detectable when the Au$^{3+}$ concentration was in the range of 40 to 160 µM (FIGS. 9A and 9B). As the Au$^{3+}$ concentration increased to 200 µM (an Au$^{3+}$:AuNP ratio of 610:1), the particle plasmon peak completely disappeared, indicating that all of the AuNPs were dissolved. It is clear that a high concentration of Au$^{3+}$ promotes quick dissolution of AuNPs at room temperature, and therefore an Au$^{3+}$:AuNP ratio of 610:1 was used in subsequent experiments.

EXAMPLE 2

Figure 10A:
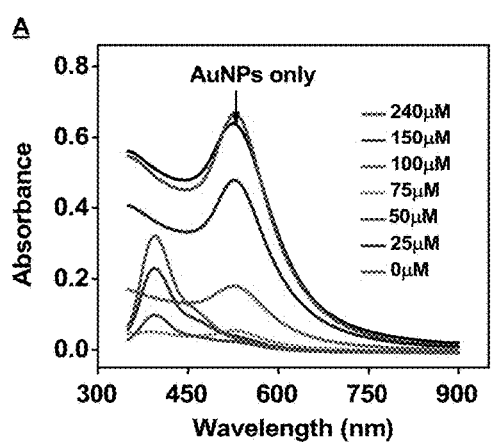
FIG. 10A shows the UV-Vis spectra recorded from 200 μM of $Au^{3+}$ in CTAB with different concentrations of NADH after a 40-min reaction with 328 picomoles of AuNPs at room temperature.
Figure 10B:
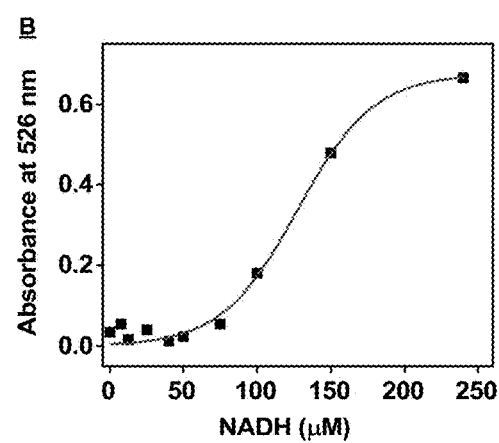
FIG. 10B depicts the absorbance measurements at 526 nm for AuNPs in the presence of different concentrations of NADH.

Au$^{3+}$ can dissolve AuNPs in an acidic CTAB solution whereas its reduced form (Au$^+$) is unable to perform such dissolution.[29] Xiao et al. previously reported that NADH facilitates the rapid reduction of Au$^{3+}$ to Au$^+$ in CTAB solution,[33] and it was therefore predicted that the presence of NADH would inhibit the dissolution of AuNPs in an Au$^{3+}$-CTAB solution. To confirm this, the effect of different concentrations of NADH on AuNP dissolution was investigated by monitoring absorbance at 526 nm. At concentrations below 75 µM, NADH reduced only a small quantity of Au$^{3+}$ to Au$^+$, and the excess Au$^{3+}$ remaining in the solution was sufficient to dissolve most of the AuNPs. The absorbance of the small quantity of AuNPs remaining in the solution under these conditions became difficult to measure accurately due to strong interference from the distinct shoulder of the Au$^{3+}$-CTAB complex at 450 nm. When the NADH concentration was in the range between 100 to 150 µM, the amount of unreacted Au$^{3+}$ in the solution only induced the partial dissolution of AuNPs. AuNPs' dissolution was further inhibited at increasing NADH concentrations. Interestingly, a higher AuNP absorbance was observed after 40 min upon addition of 240 µM NADH relative to the absorbance of undissolved AuNPs. This is because the excess NADH first fully reduced Au$^{3+}$ to Au$^+$, and then further reduced Au$^+$ to Au$^0$. This resulted in the enlargement of the AuNPs, consistent with previously-reported findings.[33] By monitoring the absorbance change at 526 nm, the NADH concentrations above 75 µM could be identified (FIGS. 10A and 10B).

EXAMPLE 3

Figure 2:
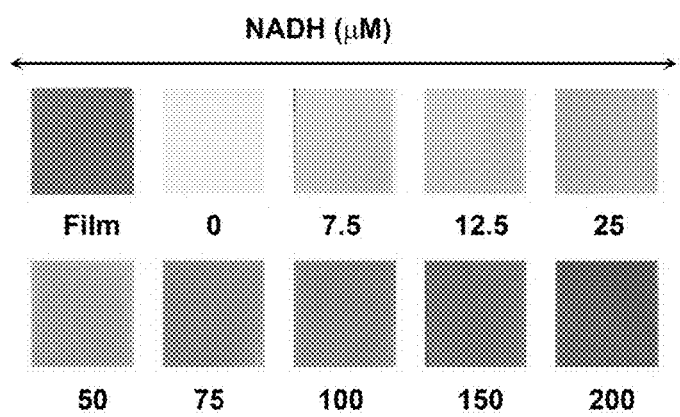
FIG. 2 shows the colorimetric detection of NADH on AuNP-coated mixed cellulose ester (MCE) filter paper in solution. Increasing the NADH concentration from 0 to 200 μM in a 200 μM $Au^{3+}$-CTAB solution increasingly inhibited the dissolution of AuNPs coated on the paper, resulting in a more intense red color readout.
Figure 11A:
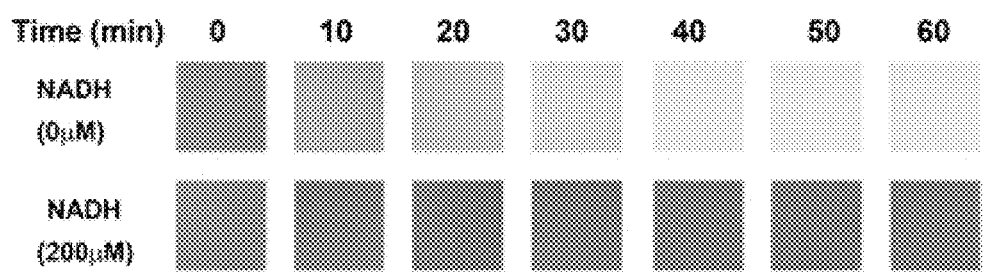
FIG. 11A depicts the colorimetric change of mixed cellulose ester (MCE) filter paper coated with AuNPs in the absence (0 μM) and presence (200 μM) of NADH in a 200 μM of $Au^{3+}$-CTAB solution.
Figure 11B:
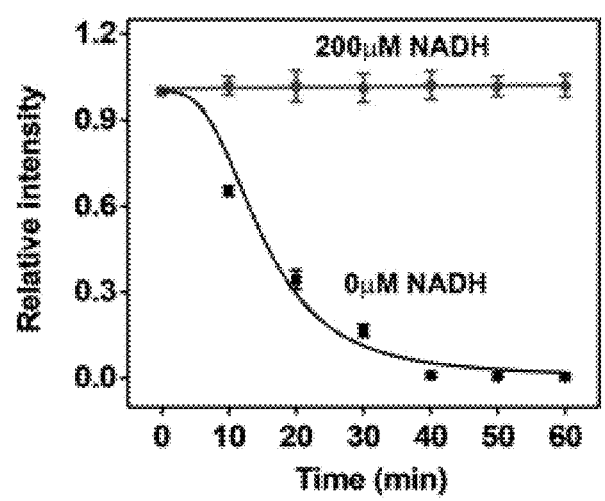
FIG. 11B is a graph showing the time course of the change in color intensity corresponding to the absence and presence of NADH on the MCE paper. The intensity of the readouts in the testing zones was measured with the ImageJ software and their respective relative intensity calculated by normalizing the unreacted AuNP film to 1 and the fully dissolved AuNP-coated film in the absence of NADH to 0.

To achieve detection in an instrument-free manner, the NADH-inhibited dissolution process was carried out on mixed cellulose ester (MCE) filter paper. The uniform pore size of MCE paper allows stable and reproducible liquid flow through the membrane, and a smooth and even AuNP layer can be rapidly formed on the MCE surface via simple vacuum filtration. This routine lab technique was used to prepare the AuNP-coated film because previous work has shown that films made by this technique generally offer good homogeneity, strong adhesive strength, massive scalability, excellent stability and reproducibility.[34,35] The films were fabricated by filtering 1.9 mL of freshly-made, citrate-capped AuNPs (771.4 picomoles particles) on MCE paper. After drying for 20 min, each film was cut into 20 squares (~21 picomoles AuNPs on each piece; 5 mm W×6 mm L) and these squares were dropped into $Au^{3+}$-CTAB solutions comprising different concentrations of NADH. It was observed that 200 µM of $Au^{3+}$-CTAB solution dissolved all of the AuNPs from the surface in the absence of NADH, leaving the paper a white color (FIG. 2). The amount of $Au^{3+}$ in the solution decreased with increasing NADH concentrations, inhibiting the dissolution of AuNPs coated on the paper and resulting in a color readout that shifted from light pink to red (FIG. 2). Time-course experiments with AuNP-coated squares in 200 µM $Au^{3+}$-CTAB solution indicated that the dissolution of AuNPs was increased with the increase of reaction time (FIGS. 11A and 11B). Although it took 40 min to complete the reaction, the color difference was readily detectable via naked-eye observation, with a detection limit of 7.5 µM—10-fold lower than the reported value of a solution-based colorimetric NADH sensor.[33]

EXAMPLE 4

The design of the paper-based sensor was subsequently optimized to further shorten the reaction time, making it possible to visualize the presence of NADH in a microliter-scale sample. To work with very small sample volumes on the AuNP-coated film, it was necessary to confine the sample within the testing zone to avoid the lateral escape of reactants. The best way to achieve such confinement is to create both a closed hydrophobic barrier on the surface of the AuNP-coated film and an underlying hydrophobic wall across the thickness of the paper. This can be done via wax printing, a rapid and inexpensive technique for large-scale production of microfluidic paper-based analytical devices.[36] However, wax printing requires a time-consuming heat penetration step and is generally difficult to form a good hydrophobic barrier across the thickness of the paper.[36] As a simple alternative, a hydrophobic barrier was formed on the surface by using a wax pencil to draw a circle on the AuNP-coated paper to confine the reactants. This wax drawing can be perfollned in five seconds with good reproducibility and no restriction on the thickness of the circle.

EXAMPLE 5

Lateral diffusion of fluids in paper is usually much more rapid than vertical diffusion.[36] When a 25 µL droplet of $Au^{3+}$-CTAB solution was placed on the AuNP-coated paper without wax confinement, it was observed that a narrow white circle formed at the edge of the droplet after 10 min, and that 46% of AuNPs dissolved in the reaction area (FIG. 12A). Most of the $Au^{3+}$-CTAB micelles, which are typically approximately 3 nm in diameter,[37] presumably migrated to the edge of the droplet due to the "coffee ring effect"[38] such that particles in this region are more likely to be dissolved than those in the center. In general, however, the wax circle confines the sample and allows vertical—but not lateral—diffusion of liquid out of the AuNP-coated testing zone. It was observed that a droplet of 25 µL of $Au^{3+}$-CTAB was successfully retained within the wax-circled test zone for up to 21 min, with 58% of the AuNPs dissolved (FIG. 12B). However, the dissolution was still restricted primarily to the edge of the wax-circled test zone while the film at the center remained intact and red. It was also observed that lateral escape of the confined reactants occurred from underneath the wax barrier.

To further eliminate lateral diffusion in the confined test zone, a hydrophilic absorbent layer was added underneath the wax-circled AuNP-coated film to enhance the vertical mass transport of reactants within the paper. Since water has at least a 10-fold higher self-diffusion coefficient[39] than CTAB micelles,[40,41] water molecules travel faster than $Au^{3+}$-CTAB micelles during capillary force-assisted vertical diffusion, resulting in greatly increased concentration of $Au^{3+}$-CTAB complex in the testing zone as water is removed by this absorbent layer. Compared with the AuNP dissolution without an absorbent layer (FIG. 13A), the capillary force significantly enhanced vertical diffusion and thereby prevented the formation of the previously observed "coffee ring" reaction pattern, resulting in more uniform dissolution with a shorter reaction time. A uniform surface reaction requires a good match between the AuNP-coated film and the absorbent layer. Different absorbent layers such as rice paper (FIG. 13B), paper towel (FIG. 13C), Kimwipe (FIG. 13D), copy paper (FIG. 13E), and cotton pads (FIG. 13F), were tested and it was found that the most uniform dissolution of AuNPs occurred with a cotton absorbent layer (FIG. 13F).

EXAMPLE 6

Figures 14A, 14B, 14C:
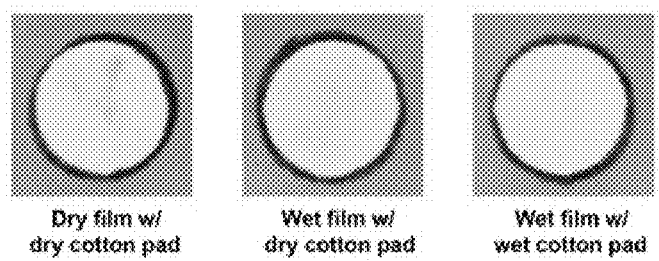
FIG. 14A shows the performance of dry wax-circled MCE paper placed in contact with dry cotton pad.
FIG. 14B shows the performance of pre-wetted MCE paper in contact with dry cotton pad.
FIG. 14C shows the performance of pre-wetted MCE paper in contact with pre-wetted cotton pad. Each test was performed with 25 μL of 200 μM $Au^{3+}$-CTAB at room temperature. The intensity of the readouts in the testing zones was measured with the ImageJ software and AuNP dissolution was calculated by normalizing the intensity of the AuNP film alone to 0% and the intensity of the MCE filter paper to 100%.

The homogeneity and speed of dissolution can be further improved by employing a "wet-on-wet" combination of wax-circled AuNP-coated film and absorbent cotton layer (FIG. 14C). Control experiments demonstrated that 25 µL it of $Au^{3+}$-CTAB solution confined in a dry AuNP-coated testing zone took 9 min to dissolve 80% of the AuNPs in combination with a dry cotton layer (FIG. 14A), whereas 90% of the AuNPs were dissolved when a pre-wetted AuNP-coated film was put on top of a dry cotton absorbent layer (FIG. 14B). It is believed that the non-uniform pattern formed on these AuNP-coated films is due to the existence of tiny air bubbles between the AuNP films and the dry cotton layer, which therefore requires more time to facilitate mass transport through the film. In contrast, when a tight contact was formed between the layers by pre-wetting both the AuNP-coated film and cotton layer (FIG. 14C), all of the AuNPs dissolved after 4 min due to uniform mass transportation.

EXAMPLE 7

It is anticipated that NADH-mediated inhibition of AuNP dissolution could enable simple and direct detection of dehydrogenase-driven NADtreduction for a number of analytes. GDH, an enzyme that converts $NAD^+$ into NADH in the presence of glucose, was chosen as a model for the device. Specifically, the glucose concentration determines the amount of NADH produced.[42] The results confirmed that NADH generated by GDH modulates the dissolution of the AuNP film in the device, generating a colorimetric readout that can be visualized within 4 min. The AuNPs in the testing zone were completely dissolved in the absence of glucose, indicating that no NADH was being produced. The amount of NADH increased with increasing glucose concentrations, and the color of the test zone changed from light pink to red as the glucose concentration increased from 2 to 20 mM (FIGS. 5A and 5B).

Figure 5A:
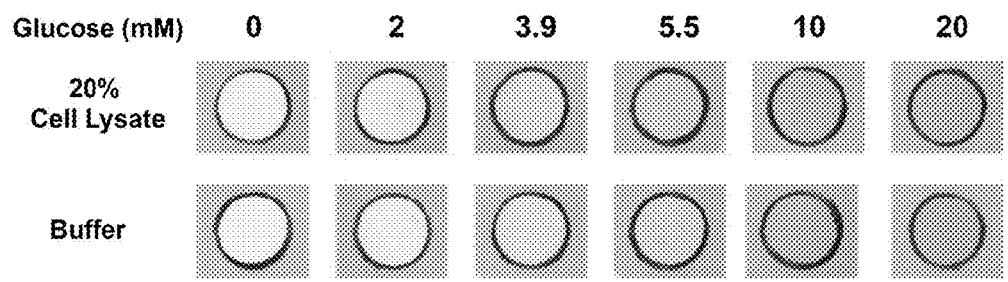
FIG. 5A shows the colorimetric readout of samples comprising different concentrations of glucose (0-20 mM) and 0.1 U glucose dehydrogenase (GDH) with 400 μM of $Au^{3+}$-CTAB in buffer and 600 μM of $Au^{3+}$-CTAB in 20% *E coli* cell lysate, respectively, after a 4-min reaction.
Figure 5B:
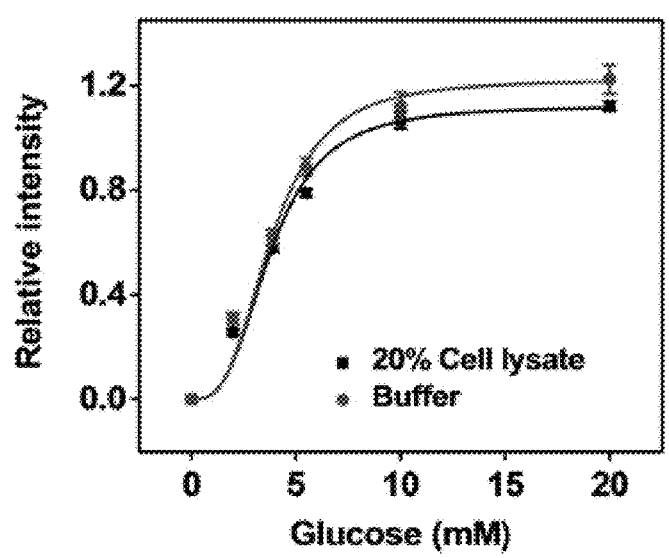
FIG. 5B depicts the intensity of the readouts in the testing zones measured with the ImageJ software and their respective relative intensity calculated by normalizing the unreacted AuNP film to 1 and the fully dissolved AuNP-coated film in the absence of glucose to 0.
Figure 16A:
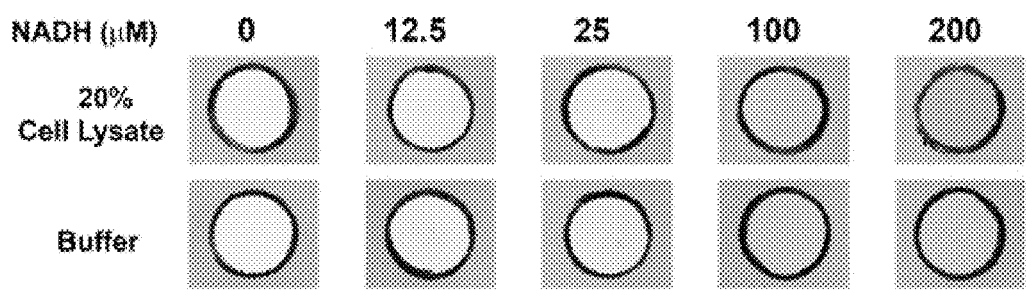
FIG. 16A shows the colorimetric changes of the paper-based device monitoring multiple concentrations of NADH with and without 20% *E coli* cell lysate in 350 μM and 200 μM of $Au^{3+}$-CTAB solution at room temperature, respectively.
Figure 16B:
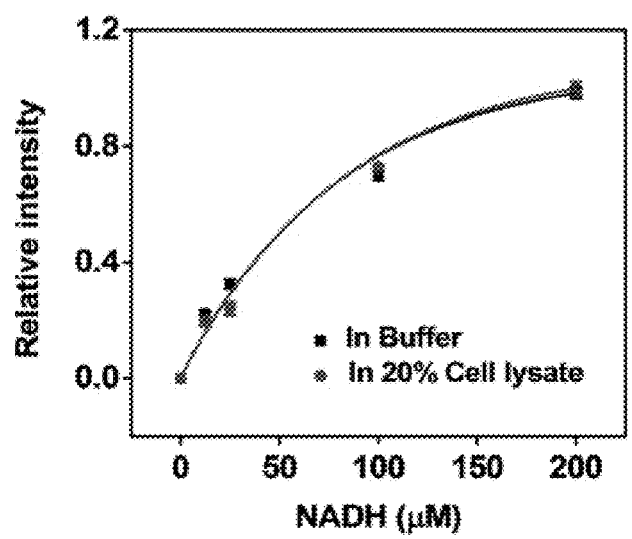
FIG. 16B demonstrates the relative intensity measured with the ImageJ software and calculated by normalizing the unreacted AuNP-coated film to 1 and the AuNP-coated film in the absence of NADH to 0.

Further experiments were performed to confirm the detection of NADH using the assembled paper-based device (FIGS. 16A and 16B) and monitor the NAD+-driven enzymatic reactions in 20% *E. coli* cell lysate (FIGS. 5A and 5B). Since *E. coli* cell lysate contains NADH, to test the reproducibility of our device, the concentration of $Au^{3+}$-CTAB was adjusted to completely dissolve the AuNPs in the test zone with 20% *E. coli* cell lysate. Experimental results demonstrated that these complex sample matrices did not measurably affect the detection results.

EXAMPLE 8

Figure 6A:
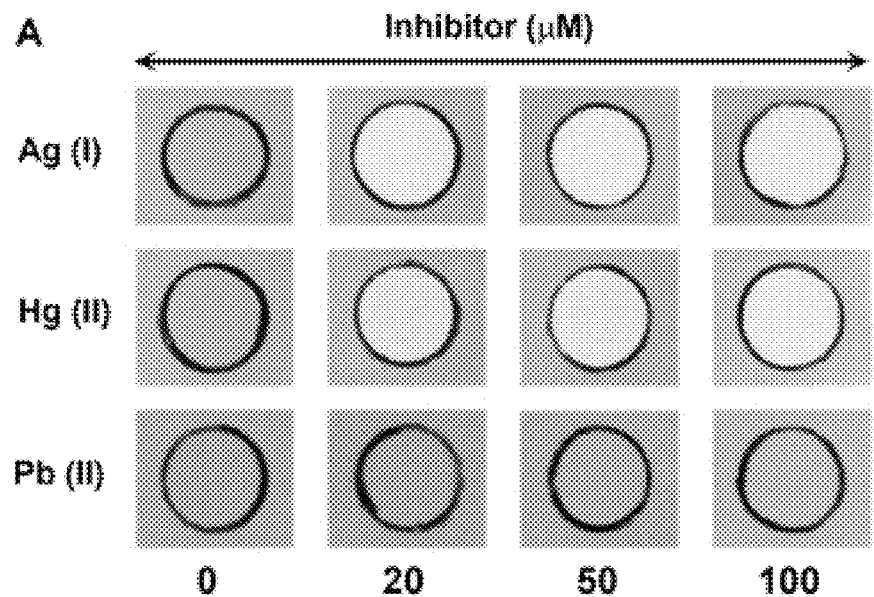
FIG. 6A demonstrates the result of screening the inhibitory effects of various heavy metal ions on GDH-driven NADH production. An exemplary paper-based device was used to measure NADH production by 0.1 U GDH in a 25-μL sample comprising different concentrations (0-100 μM) of heavy metal ions in 400 μM of $Au^{3+}$-CTAB after a 4-min reaction.
Figure 6B:
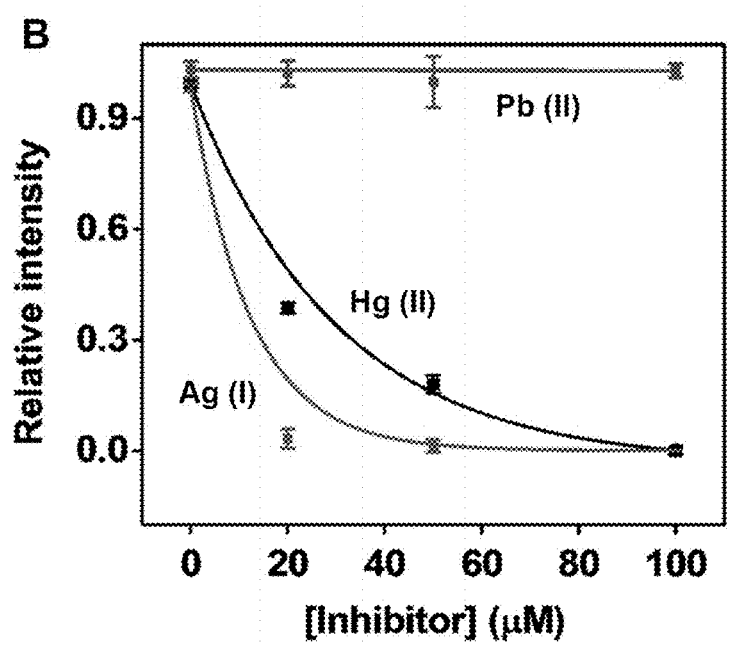
FIG. 6B depicts the intensity of the readouts in the testing zones for each heavy metal ion, Ag(I), Hg(II), and Pb(II), respectively, measured with the ImageJ software and their respective relative intensity calculated by normalizing the unreacted AuNP film to 1 and the fully dissolved AuNP-coated film in the presence of 100 μM of Ag(I) to 0.

Heavy metal ions such as Ag(I) and Hg(II) are strong inhibitors of GDH, whereas Pb(II) has been reported to have no inhibitory effect on the GDH reaction.[43] To demonstrate the ability of this device to screen for enzyme inhibitors, the effects of Ag(I), Hg(II), and Pb(II) on GDH-driven NADH production were tested. In the presence of 20 μM or higher of Ag(I), the activity of GDH was completely inhibited and no NADH was generated, yielding a completely white readout (FIG. 6B, Ag(I)). GDH activity was also significantly inhibited by 20 μM of Hg(II), although the enzyme still generated a very small amount of NADH that resulted in approximately 30% inhibition of AuNPs dissolution, yielding a light pink color in the testing zone. Clearly, the GDH inhibition and AuNPs dissolution was increased with increasing Hg(II) concentration, with complete dissolution of AuNPs in the testing zone at a Hg(II) ion concentration of 100 μM (FIG. 6B, Hg(II)). As expected, no dissolution of AuNPs was observed in the testing zone in the presence of Pb(II) at concentrations ranging between 20 and 100 μM (FIG. 6B, Pb(II)). This confirmed that Pb(II) has no inhibitory effect on GDH, which is consistent with the literature.[43]

To demonstrate the inhibitory effects of different concentrations of Hg(II) on GDH-driven NADH-production, the enzymatic reactions with Hg(II) concentration ranging from 0 to 200 μM were performed. The resulting solution was then added into a 400 μM of $Au^{3+}$-CTAB solution, and 25 μL of this mixture were immediately applied to the testing zone. In the absence of Hg(II), GDH fully converted $NAD^+$ into NADH after 4 minutes, completely inhibiting AuNP dissolution and leaving the testing zone dark red (FIG. 17A). In the presence of 2.5 μM of Hg(II), enzyme activity was slightly inhibited, and a small decrease of color intensity in the testing zone was observed. GDH-mediated production of NADH decreased in parallel with the increase of Hg(II) concentration, yielding a lighter readout as increased dissolution of AuNPs occurred (FIG. 17A). At a Hg(II) concentration of 100 μM, a completely white readout was observed within the wax-circled test zone, indicating complete inhibition of GDH and dissolution of AuNPs (FIG. 17A). The color intensity was measured with the ImageJ software and the normalized intensity with different concentrations of Hg(II) was plotted (FIG. 17B). The kinetics of GDH in homogeneous solution was also monitored with or without Hg(II) ions (FIG. 18). Enzyme activity was calculated based on the kinetics of the enzymatic reaction and defined as 100% in the absence of Hg(II). Based on this analysis, an $IC_{50}$ value of 20 μM was calculated for this ion on the paper-based device, which is consistent with its $IC_{50}$ value obtained in homogeneous solution (18 μM).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

1. Ying, W. $NAD^+$/NADH and $NADP^+$/NADPH in Cellular Functions and Cell Death: Regulation and Biological Consequences. *Antioxid. Redox Signaling.* 2008, 10, 179-206.
2. Jaegfeldt, H.; Kuwana, T.; Johansson, G. Electrochemical Stability of Catechols with a Pyrene Side Chain Strongly Adsorbed on Graphite Electrodes for Catalytic Oxidation of Dihydronicotinamide Adenine Dinucleotide. *J. Am. Chem. Soc.* 1983, 105, 1805-1814.
3. Wu, Q.; Maskus, M.; Pariente, F.; Tobalina, F.; Fernández, V. M.; Lorenzo, E.; Abruña, H. D. Electrocatalytic Oxidation of NADH at Glassy Carbon Electrodes Modified with Transition Metal Complexes Containing 1,10-Phenanthroline-5,6-dione Ligands. *Anal. Chem.* 1996, 68, 3688-3696.
4. Koppaka, V.; Thompson, D. C.; Chen, Y.; Ellermann, M.; Nicolaou, K. C.; Juvonen, R. O.; Petersen, D.; Deitrich, R. A.; Hurley, T. D.; Vasiliou, V. Aldehyde Dehydrogenase Inhibitors: a Comprehensive Review of the Pharmacology, Mechanism of Action, Substrate Specificity, and Clinical Application. *Pharmacol. Rev.* 2012, 64, 520-539.
5. Tanei, T.; Morimoto, K.; Shimazu, K.; Kim, S. J.; Tanji, Y.; Taguchi, T.; Tamaki, Y.; Noguchi, S. Association of Breast Cancer Stem Cells Identified by Aldehyde Dehydrogenase 1 Expression with Resistance to Sequential Paclitaxel and Epirubicin-Based Chemotherapy for Breast Cancers. *Clin. Cancer Res.* 2009, 15, 4234-4241.
6. Deng, S.; Yang, X.; Lassus, H.; Liang, S.; Kaur, S.; Ye, Q.; Li, C.; Wang, L. P.; Roby, K. F.; Orsulic, S.; Connolly, D. C.; Zhang, Y.; Montone, K.; Butzow, R.; Coukos, G.; Zhang, L. Distinct Expression Levels and Patterns of Stem Cell Marker, Aldehyde Dehydrogenase Isoform 1 (ALDH1), in Human Epithelial Cancers. *PloS One* 2010, 5, e10277.
7. Robins, R. K. Nucleoside and Nucleotide Inhibitors of Inosine Monophosphate (IMP) Dehydrogenase as Potential Antitumor Inhibitors. *Nucleosides Nucleotides* 1982, 1, 35-44.
8. Arolfo, M. P.; Overstreet, D. H.; Yao, L.; Fan, P.; Lawrence, A. J.; Tao, G.; Keung, W.-M.; Vallee, B. L.; Olive, M. F.; Gass, J. T.; Rubin, E.; Anni, H.; Hodge, C. W.; Besheer, J.; Zablocki, J.; Leung, K.; Blackburn, B. K.; Lange, L. G.; Diamond, I. Suppression of Heavy Drinking and Alcohol Seeking by a Selective ALDH-2 Inhibitor. *Alcohol.: Clin. Exp. Res.* 2009, 33, 1935-1944.
9. Yao, L.; Fan, P.; Arolfo, M.; Jiang, Z.; Olive, M. F.; Zablocki, J.; Sun, H.-L.; Chu, N.; Lee, J.; Kim, H.-Y.;

9. Leung, K.; Shryock, J.; Blackburn, B.; Diamond, I. Inhibition of Aldehyde Dehydrogenase-2 Suppresses Cocaine Seeking by Generating THP, a Cocaine Use-Dependent Inhibitor of Dopamine Synthesis. *Nat. Med.* 2010, 16, 1024-1028.
10. Overstreet, D. H.; Knapp, D. J.; Breese, G. R.; Diamond, I. A Selective ALDH-2 Inhibitor Reduces Anxiety in Rats. *Pharmacol., Biochem. Behav.* 2009, 94, 255-261.
11. Hilton, J. Role of Aldehyde Dehydrogenase in Cyclophosphamide-Resistant L1210 Leukemia. *Cancer Res.* 1984, 44, 5156-5160.
12. Granchi, C.; Roy, S.; Giacomelli, C.; Macchia, M.; Tuccinardi, T.; Martinelli, A.; Lanza, M.; Betti, L.; Giannaccini, G.; Lucacchini, A.; Funel, N.; Leon, L. G.; Giovannetti, E.; Peters, G. J.; Palchaudhuri, R.; Calvaresi, E. C.; Hergenrother, P. J.; Minutolo, F. Discovery of N-Hydroxyindole-Based Inhibitors of Human Lactate Dehydrogenase Isoform A (LDH-A) as Starvation Agents against Cancer Cells. *J. Med. Chem.* 2011, 54, 1599-1612.
13. Birkenstock, T.; Liebeke, M.; Winstel, V.; Krismer, B.; Gekeler, C.; Niemiec, M. J.; Bisswanger, H.; Lalk, M.; Peschel, A. Exometabolome Analysis Identifies Pyruvate Dehydrogenase as a Target for the Antibiotic Triphenylbismuthdichloride in Multiresistant Bacterial Pathogens. *J. Biol. Chem.* 2012, 287, 2887-2895.
14. Degli Esposti, M. Inhibitors of NADHUbiquinone reductase: an overview. *Biochim. Biophys. Acta* 1998, 1364, 222-235.
15. Jain, P. K.; El-Sayed, I. H.; El-Sayed, M. A. Au Nanoparticles Target Cancer. *Nano Today* 2007, 2, 18-29.
16. Medley, C. D.; Smith, J. E.; Tang, Z.; Wu, Y.; Bamrungsap, S.; Tan, W. Gold Nanoparticle-Based Colorimetric Assay for the Direct Detection of Cancerous Cells. *Anal. Chem.* 2008, 80, 1067-1072.
17. Ghosh, P.; Han, G.; De, M.; Kim, C. K.; Rotello, V. M. Gold Nanoparticles in Delivery Applications. *Adv. Drug Delivery Rev.* 2008, 60, 1307-1315.
18. El-Sayed, I. H.; Huang, X.; El-Sayed, M. A. Surface Plasmon Resonance Scattering and Absorption of Anti-EGFR Antibody Conjugated Gold Nanoparticles in Cancer Diagnostics: Applications in Oral Cancer *Nano Lett.* 2005, 5, 829-834.
19. Murphy, C. J.; Gole, A. M.; Stone, J. W.; Sisco, P. N.; Alkilany, A. M.; Goldsmith, E. C.; Baxter, Gold Nanoparticles in Biology: Beyond Toxicity to Cellular Imaging. S. C. *Acc. Chem. Res.* 2008, 41, 1721-1730.
20. Jain, S.; Hirst, D. G.; O'Sullivan, J. M. Gold nanoparticles as Novel Agents for Cancer Therapy. *Br. J. Radiol.* 2012, 85, 101-113.
21. Saha, K.; Agasti, S. S.; Kim, C.; Li, X. N.; Rotello, V. M.; Gold Nanoparticles in Chemical and Biological Sensing. *Chem. Rev.* 2012, 112, 2739-2779.
22. Link, S.; El-Sayed, M. A. Size and Temperature Dependence of the Plasmon Absorption of Colloidal Gold Nanoparticles. *J. Phys. Chem. B* 1999, 103, 4212-4217.
23. Henglein, A. Physicochemical Properties of Small Metal Particles in Solution: "Microelectrode" Reactions, Chemisorption, Composite Metal Particles, and the Atom-to-Metal Transition. *J. Phys. Chem.* 1993, 97, 5457-5471.
24. Valden, M.; Lai, X.; Goodman, D. W. Onset of Catalytic Activity of Gold Clusters on Titania with the Appearance of Nonmetallic Properties. *Science* 1998, 281, 1647-1650.
25. Pan, Y.; Neuss, S.; Leifert, A.; Fischler, M.; Wen, F.; Simon, U.; Schmid, G.; Brandau, W.; Jahnen-Dechent, W. Size-Dependent Cytotoxicity of Gold Nanoparticles. *Small* 2007, 3, 1941-1949.
26. Qian, K.; Sweeny, B. C.; Johnston-Peck, A. C.; Niu, W.; Graham, J. O.; Duchene, J. S.; Qiu, J.; Wang, Y. C.; Engelhard, M. H.; Su, D.; Stach, E. A.; Wei, W. D. Surface Plasmon-Driven Water Reduction: Gold Nanoparticle Size Matters. *J. Am. Chem. Soc.* 2014, 136, 9842-9845.
27. Sreeprasad, T. S.; Samal, A. K.; Pradeep, T. Body- or Tip-Controlled Reactivity of Gold Nanorods and Their Conversion to Particles through Other Anisotropic Structures. *Langmuir* 2007, 23, 9463-9471.
28. Busbee, B. D.; Obare, S. O.; Murphy, C. J. An Improved Synthesis of High-Aspect-Ratio Gold Nanorods. *Adv. Mater.* 2003, 15, 414-416.
29. Rodríguez-Fernández, J.; Pérez-Juste, J.; Mulvaney, P.; Liz-Marzán, L. M. Spatially-Directed Oxidation of Gold Nanoparticles by Au(III)-CTAB Complexes. *J. Phys. Chem. B* 2005, 109, 14257-14261.
30. Ivanova, O. S.; Zamborini, F. P. Electrochemical Size Discrimination of Gold Nanoparticles Attached to Glass/IndiumTin-Oxide Electrodes by Oxidation in Bromide-Containing Electrolyte. *Anal. Chem.* 2010, 82, 5844-5850.
31. Cifuentes, A.; Bernal, J. L.; Diez-Masa, J. C. Determination of Critical Micelle Concentration Values Using Capillary Electrophoresis Instrumentation. *Anal. Chem.* 1997, 69, 4271-4274.
32. Mortier, T.; Persoons, A.; Verbiest, T. Oxidation of Solid Gold in Chloroform Solutions of Cetyltrimethylammonium Bromide. *Inorg. Chem. Commun.* 2005, 8, 1075-1077.
33. Xiao, Y.; Pavlov, V.; Levine, S.; Niazov, T.; Markovitch, G.; Willner, I. Catalytic Growth of Au Nanoparticles by NAD(P)H Cofactors: Optical Sensors for NAD(P)$^+$-Dependent Biocatalyzed Transformations. *Angew. Chem.* 2004, 116, 4619-4622.
34. Wu, Z.; Chen, Z.; Du, X.; Logan, J. M.; Sippel, J.; Nikolou, M.; Kamaras, K.; Reynolds, J. R.; Tanner, D. B.; Hebard, A. F.; Rinzler, A. G. Transparent, Conductive Carbon Nanotube Films. *Science* 2004, 305, 1273-1276.
35. Lee, J. H.; Kong, B. S.; Baek, Y. K.; Yang, S. B.; Jung, H. T. Tin Nanoparticle Thin Film Electrodes Fabricated by the Vacuum Filtration Method for Enhanced Battery Performance. *Nanotechnology* 2009, 20, 235203.
36. Carrilho, E.; Martinez, A. W.; Whitesides, G. M. Understanding Wax Printing: A Simple Micropatterning Process for Paper-Based Microfluidics. *Anal. Chem.* 2009, 81, 7091-7095.
37. Dorshow, R.; Briggs, J.; Bunton, C. A.; Nicoli, D. F. Dynamic Light Scattering from Cetyltrimethylammonium Bromide Micelles: Intermicellar Interactions at Low Ionic Strengths. *J. Phys. Chem.* 1982, 86, 2388-2395.
38. Deegan, R. D.; Bakajin, O.; Dupont, T. F.; Huber, G.; Nagel, S. R.; Witten, T. A. Capillary Flow as the Cause of Ring Stains From Dried Liquid Drops. *Nature* 1997, 389, 827-829.
39. Mills, R. Self-diffusion in Normal and Heavy Water in the Range 1-45.deg. *J. Phys. Chem.* 1973, 77, 685-688.
40. Lindman, B.; Puyal, M.-C.; Kamerka, N.; Rymden, R.; Stilbs, P. Micelle Formation of Anionic and Cationic Surfactants from Fourier Transform Hydrogen-1 and Lithium-7 Nuclear Magnetic Resonance and Tracer Self-Diffusion Studies. *J. Phys. Chem.* 1984, 88, 5048-5057.
41. Otto, W. H.; Britten, D. J.; Larive, C. K. NMR Diffusion Analysis of SurfactantHumic Substance Interactions. *J. Colloid Interface Sci,* 2003, 261, 508-513.

42. Zhang, M.; Smith, A.; Gorski, W. Carbon Nanotube-Chitosan System for Electrochemical Sensing Based on Dehydrogenase Enzymes. *Anal. Chem.* 2004, 76, 5045-5050.

43. Kobayashi, Y.; Horikoshi, K. Purification and Properties of NAD-Dependent D-Glucose Dehydrogenase Produced by Alkalophilic *Corynebacterium* sp. No. 93-1. *Agric. Biol. Chem.* 1980, 44, 2261-2269.

What is claimed is:

1. A device for detecting the presence of an electron donor in a sample, comprising a first cover layer, at least one testing zone provided on a porous membrane, exposed by a void in the first cover layer and confined by a barrier that is impermeable to the sample and prevents lateral diffusion of the sample across the barrier, said at least one testing zone comprising a surface immobilized with metallic nanoparticles at said at least one testing zone, and a second cover layer provided beneath the porous membrane, which is impermeable to the sample.

2. The device according to claim 1, wherein the porous membrane comprises mixed cellulose ester paper.

3. The device according to claim 1, further comprising an absorbent layer provided between the porous membrane and the second cover layer, the absorbent layer substantially assisting the vertical diffusion of the sample through the porous membrane.

4. The device according to claim 1, wherein the metallic nanoparticles comprise a metal selected from gold, silver, copper, and platinum.

5. The device according to claim 1, capable of detecting the presence of the electron donor at less than 200 µM.

6. The device according to claim 5, capable of detecting the presence of the electron donor at less than 12.5 µM.

7. The device according to claim 1, wherein the barrier comprises a substance substantially insoluble in water.

8. The device according to claim 7, wherein the substance substantially insoluble in water is wax.

9. A method of detecting the presence of an electron donor, comprising providing a device according to claim 1, providing a sample for at least one testing zone of the device, the sample comprising at least one salt of the same metal as the nanoparticles, each testing zone being confined by a closed barrier substantially impermeable to the sample, wherein an inhibition of the nanoparticles' dissolution indicating the presence of the electron donor.

10. The method according to claim 9, wherein the electron donor is produced by a dehydrogenase enzyme/enzyme substrate pair in the presence of an electron acceptor.

11. The method according to claim 9, wherein the metal is selected from gold, silver, copper, and platinum.

12. The method according to claim 9, wherein the sample further comprises cetyltrimethylammonium and a halogen-based counterion.

13. The method according to claim 9, further comprising providing an absorbent layer disposed between the porous membrane and the second cover layer, the absorbent layer substantially assisting the vertical diffusion of the sample through the porous membrane.

14. The method according to claim 9, wherein the inhibition of the nanoparticles' dissolution results in a colorimetric change visible to the naked eyes.

15. The method according to claim 9, wherein the device detects less than 200 µM of the electron donor.

16. The method according to claim 15, wherein the device detects less than 12.5 µM of the electron donor.

17. A device for detecting the presence of dihydronicotinamide adenine dinucleotide or, alternatively, dihydronicotinamide adenine dinucleotide phosphate, in a sample, comprising a first cover layer, at least one testing zone provided on mixed cellulose ester paper and exposed by a void in the first cover layer, said at least one testing zone comprising a surface immobilized with gold nanoparticles at said at least one testing zone and bound by a barrier substantially impermeable to the sample, such that the barrier prevents lateral diffusion of the sample across the barrier, an absorbent layer provided beneath the mixed cellulose ester paper, and a second cover layer provided beneath the absorbent layer, which is impermeable to the sample.

18. The device according to claim 17, wherein the barrier comprises a substance substantially insoluble in water.

19. The device according to claim 18, wherein the substance substantially insoluble in water is wax.

* * * * *